(12) United States Patent
Fletcher et al.

(10) Patent No.: US 7,077,858 B2
(45) Date of Patent: Jul. 18, 2006

(54) FLEXIBLE HEAT EXCHANGERS FOR MEDICAL COOLING AND WARMING APPLICATIONS

(75) Inventors: R. David Fletcher, White Rock (CA); Yunquan Chen, Delta (CA)

(73) Assignee: Coolhead Technologies, Inc., Delta (CA)

( * ) Notice: Subject to any disclaimer, the term of this patent is extended or adjusted under 35 U.S.C. 154(b) by 80 days.

(21) Appl. No.: 10/665,073

(22) Filed: Sep. 22, 2003

(65) Prior Publication Data

US 2005/0065581 A1   Mar. 24, 2005

(51) Int. Cl.
*A61F 7/00*   (2006.01)

(52) U.S. Cl. ........................ 607/104; 607/108

(58) Field of Classification Search ............. 607/104, 607/108–12, 114; 165/46, 80.4, 185
See application file for complete search history.

(56) References Cited

U.S. PATENT DOCUMENTS

| | | | |
|---|---|---|---|
| 4,098,279 A | 7/1978 | Golden | |
| 4,108,146 A | 8/1978 | Golden | |
| 4,750,493 A | 6/1988 | Brader | 128/380 |
| 4,846,176 A | 7/1989 | Golden | |
| 4,910,978 A | 3/1990 | Gorden et al. | 62/530 |
| 4,962,761 A | 10/1990 | Golden | |
| 5,057,964 A | 10/1991 | Bender et al. | 361/118 |
| 5,190,032 A | 3/1993 | Zacoi | 128/400 |
| 5,269,369 A | 12/1993 | Faghri | |
| 5,368,093 A | 11/1994 | Takehashi | 165/46 |
| 5,486,204 A | 1/1996 | Clifton | 607/96 |
| 5,643,336 A | 7/1997 | Lopez-Claros | 607/104 |
| 5,653,741 A | 8/1997 | Grant | |
| 5,660,917 A | 8/1997 | Fujimori et al. | 428/195 |
| 5,757,615 A | 5/1998 | Donahoe et al. | 361/687 |
| 5,897,581 A | 4/1999 | Fronda et al. | 607/109 |
| 5,913,855 A | 6/1999 | Gough et al. | 606/41 |
| 5,916,242 A | 6/1999 | Schwartz | 607/113 |
| 6,030,412 A | 2/2000 | Klatz et al. | 607/104 |
| 6,197,045 B1 | 3/2001 | Carson | 607/104 |
| 6,367,541 B1 | 4/2002 | McCullough | 165/803 |
| 6,375,674 B1 | 4/2002 | Carson | 607/104 |
| 6,511,502 B1 | 1/2003 | Fletcher | 607/109 |
| 6,549,411 B1 | 4/2003 | Herbert | 361/704 |
| 6,551,347 B1 | 4/2003 | Elkins | 607/104 |

FOREIGN PATENT DOCUMENTS

JP   2004105589   4/2004

*Primary Examiner*—Roy D. Gibson
*Assistant Examiner*—Aaron Roane
(74) *Attorney, Agent, or Firm*—Oyen Wiggs Green & Mutala LLP

(57) ABSTRACT

A flexible heat exchanger is suitable for heating or cooling living subjects. The heat exchanger has a a volume having at least one inlet for receiving a heat exchange fluid and at least one outlet. A flexible heat exchange plate that isessentially impermeable to the heat exchange fluid is penetrated by substantially rigid thermally conductive members. The members provide paths of high thermal conductivity through the plate. The heat exchange fluid may be water.

29 Claims, 10 Drawing Sheets

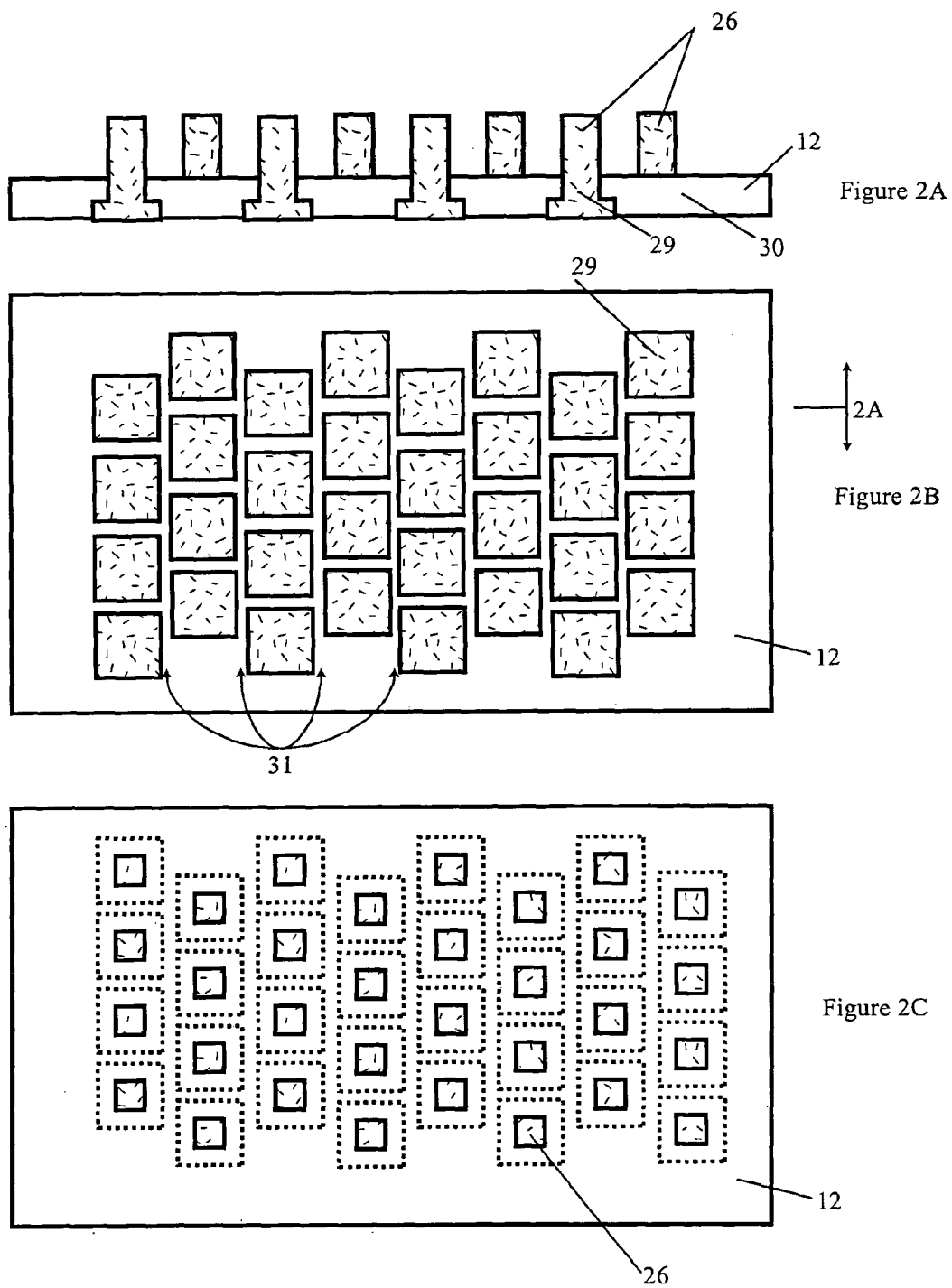

FLEXIBLE HEAT EXCHANGERS FOR MEDICAL COOLING AND WARMING APPLICATIONS

TECHNICAL FIELD

The invention relates to heat exchangers. The invention has particular application in warming or cooling living subjects. The invention may be applied to cooling the brains or other body parts of living subjects.

BACKGROUND

It has been discovered that quickly inducing hypothermia can significantly improve the recovery prospects of patients who suffer global ischemic brain injury secondary to cardiac arrest and probably focal ischemic brain injury from thrombotic or embolic causes. The latter is referred to as an ischemic stroke. Some trials have placed global and focal ischemic brain damaged victims in whole-body cooling chambers or devices. Intra vascular devices are used for whole body cooling and, secondarily, brain cooling. Such chambers or devices are unwieldy and can be intimidating for the patient. Fletcher, U.S. Pat. No. 6,511,502 discloses methods for cooling a subject's brain by applying heat exchangers to the neck of the subject adjacent the subject's carotid arteries. The heat exchangers cool blood flowing to the subject's brain.

In various other areas of medicine it is desirable to cool body parts. Prior U.S. patents which relate to cooling body parts include: U.S. Pat. Nos. 5,916,242; 4,566,455; 4,750,493; 4,763,866; 4,020,963; 5,190,032; 5,486,204; 5,643,336; 5,897,581; 5,913,855; 5,057,964; and 6,030,412.

Various types of heat exchanger exist. Air cooled heat sinks are structures which take heat from an object and dissipate the heat into ambient air. Such heat sinks typically consist of a finned piece of thermally conductive material having a face which can be placed in thermal contact with an object, such as an electronic component, to be cooled. Some heat sinks are equipped with fans located to flow air past the fins to improve the rate at which heat is dissipated.

U.S. Pat. No. 6,549,411 B1 discloses a flexible heat sink that can be attached to a generally flat surface of an object. The heat sink can flex to conform to the surface of the object to achieve improved contact with the object, and hence increase the efficiency of heat transfer between the heat sink and the object. U.S. Pat. No. 6,367,541 B2 discloses a heat sink that can be attached to multiple electronic chips which have different heights. The heat sink dissipates heat from the chips into ambient air. The devices disclosed in these patents are not suitable for heating or cooling living subjects.

U.S. Pat. No. 5,368,093 discloses a flexible bag filled with thermal transfer fluid useful for thawing frozen foods. U.S. Pat. No. 4,910,978 discloses a flexible pack containing a gel. The pack can be cooled and applied to a patient for cold therapy. The pack conforms to surface contours of the patient's body. These devices have limited cooling capacities.

More sophisticated heat exchangers use a heat exchange fluid such as a cooling or heating liquid instead of ambient air to carry heat away from or provide heat to an object to be cooled or heated. U.S. Pat. No. 5,757,615 discloses a flexible heat exchanger with circulating water as coolant for cooling a notebook computer. U.S. Pat. No. 5,643,336 discloses a flexible heating or cooling pad with circulating fluid for therapeutically treating the orbital, frontal, nasal and peri-oral regions of a patient's head. U.S. Pat. No. 6,551,347 B1 discloses a flexible heat exchange structure having fluid-conducting channels formed between two layers of flexible material for heat/cold and pressure therapy. U.S. Pat. Nos. 6,197,045 B1 and 6,375,674 B1 disclose a flexible medical pad with an adhesive surface for adhering the pad to the skin of a patient. U.S. Pat. No. 6,030,412 discloses a flexible enveloping member for enveloping a head, neck, and upper back of a mammal for cooling the brain of the mammal suffering a brain injury. All of these heat exchangers require heat to pass through a layer of some flexible material such as rubber, or a flexible plastic such as polyurethane. In addition, heat is exchanged between the surface of the flexible material and circulating fluid. Water is the most commonly used circulating fluid.

U.S. Pat. No. 3,825,063 discloses a heat exchanger having metal screens of fine mesh with internal plastic barriers that at least partly penetrate the screens. The screens are stacked to provide transverse heat conduction relative to longitudinal flow paths. U.S. Pat. No. 4,403,653 discloses a heat transfer panel comprising a woven wire mesh core embedded in a layer of plastic material. The mesh and closure layer extend in the same longitudinal direction. U.S. Pat. No. 5,660,917 discloses a sheet with electrically insulating thermal conductors embedded in it. The apparatus disclosed in those patents is not adapted for warming or cooling living subjects.

Rubber and flexible plastics are poor conductors of heat exchangers. To provide a high heat transfer efficiency in a flexible heat exchanger in which heat is transferred across a layer of rubber or plastic the layer must be very thin. This makes such heat exchangers prone to damage. In addition, water is a poor heat conductor. Heat exchange between the flexible material and water is largely dependent on convection. Water flowing over a relatively flat surface will not result in efficient heat exchange.

There remains a need for heat exchangers suitable for warming or cooling a living subject(s) via the subject's skin surface. There is a particular need for such heat exchangers that have high ratio of heat-transfer capacity to skin contact area. There is also a need for heat exchangers which can be used in practicing the methods described in Fletcher, U.S. Pat. No. 6,511,502 and which avoid at least some disadvantages of prior heat exchangers.

SUMMARY OF THE INVENTION

The invention relates to heat exchangers. One aspect of the invention provides a flexible heat exchanger. The heat exchanger comprises a volume having at least one inlet for receiving a heat exchange fluid and at least one outlet. A heat exchange fluid, for example, water, can flow through the volume. A flexible heat exchange plate essentially impermeable to the heat exchange fluid has a plurality of substantially rigid thermally conductive members. The thermally conductive members extend through a flexible material of the plate from an outside surface of the plate into the volume. The thermally conductive members conduct heat between a subject and the heat exchange fluid.

In some embodiments the volume is defined between the plate and a flexible back wall spaced apart from the plate. The thermally conductive elements are arranged in an arrangement which permits the plate to flex to conform to surface contours of the subject.

In preferred embodiments the thermally conductive members each have a thermal conductivity of at least 50 $Wm^{-1} K^{-1}$ and preferably at least 100 $Wm^{-1} K^{-1}$. The thermally conductive elements may be made of materials such as aluminum, copper, gold, silver, alloys of two or more of aluminum, copper, gold, or silver with one another, alloys of one or more of aluminum, copper, gold, or silver with one or more other metals, carbon, graphite, diamond, or sapphire.

The thermally conductive members may cover a substantial portion of the outer surface of the flexible heat exchange plate. For example, the thermally conductive members may be exposed in an area of at least 50%, preferably at least 70% and, in some embodiments, at least 80% of an area of the flexible heat exchange plate.

The flexible material of the plate may comprise an elastomer material. The thermally conductive members may be embedded in the elastomer material by any suitable process. The elastomer material may comprise, for example, natural rubber, polyurethane, polypropylene, polyethylene, ethylene-vinyl acetate, polyvinyl chloride, silicone, or a combination of two or more of polyurethane, polypropylene, polyethylene, ethylene-vinyl acetate, polyvinyl chloride, and silicone. In some embodiments the elastomer material has a thermal conductivity not exceeding 5 $Wm^{-1} K^{-1}$.

Another aspect of the invention provides systems for heating or cooling a subject. The systems have a reservoir holding heat exchange fluid and a pair of feed pumps. One feed pump is connected to deliver the heat exchange fluid to a heat exchanger. Another feed pump is connected to withdraw the heat exchange fluid from the heat exchanger. The rate at which the heat exchange fluid is introduced into the heat exchanger by the first fed pump is balanced with the rate at which fluid is withdrawn from the heat exchanger by the second feed pump to maintain a pressure within a volume in the heat exchanger within a desired range of an ambient pressure.

Further aspects of the invention and features of specific embodiments of the invention are described below.

BRIEF DESCRIPTION OF THE DRAWINGS

In drawings which illustrate non-limiting embodiments of the invention:

FIGS. 2A, 2B and 2C are respectively a cross-section view; a bottom view; and a top view of the flexible heat exchange plate of a heat exchanger according to an alternative embodiment of the invention;

DESCRIPTION

Figure 1A:
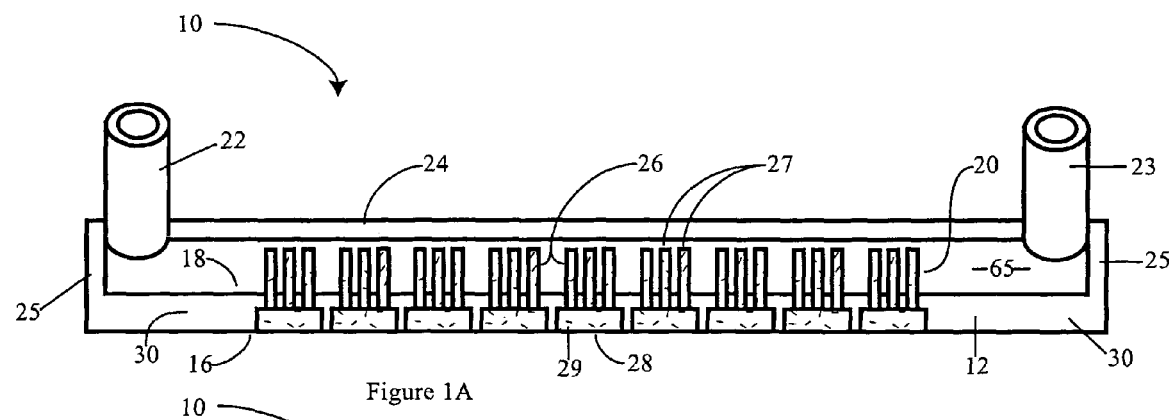
FIGS. 1A, 1B and 1C are respectively a longitudinal elevational cross-section view; a top plan view and a bottom plan view of a flexible heat exchanger configured as a cooling/warming pad for a subject's neck

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Some embodiments of this invention provide flexible heat exchangers suitable for use in warming or cooling living subjects. Heat exchangers according to the invention have a flexible heat exchange plate. A plurality of thermal channels pass through the flexible heat exchange plate. The flexible heat exchange plate has a plurality of thermally conductive members projecting through a flexible fluid essentially impermeable medium that is essentially fluid-impermeable. The thermally conductive members provide higher-temperature effective means to accept heat from a higher-temperature side, channel the heat through the medium, and release the heat on a lower-temperature side of the flexible heat exchange plate.

An outer side of the flexible heat exchange plate can be brought into contact with a living subject. In preferred embodiments, an inner side of the flexible heat exchange plate forms one side of a channel which carries a heat exchange fluid.

The thermally conductive members may be made of any suitable thermally conductive materials including thermally conductive metals, for example, aluminum, copper, gold, silver, or alloys of these metals with one another and with other metals. The thermally conductive members may also be made of non-metals which have high thermal conductivities such as carbon, suitable grades of graphite, diamond, sapphire or the like. Preferably the thermally conductive members are made from materials having thermal conductivities, k, of at least 50 $Wm^{-1}K^{-1}$ and preferably at least 100 $Wm^{-1}K^{-1}$.

The thermally conductive members are sized and located to permit the thermally conductive plate to be flexed sufficiently to conform substantially to a part of a body of a living subject. The thermally conductive members are dimensioned and distributed in a manner so that the thermally conductive members cover a large proportion of the area of the outer side of the flexible heat exchange plate. In certain embodiments of the invention a plurality of the thermally conductive members cover at least 50%, preferably at least 70%, and most preferably at least 80% of an area of the outer side of the flexible heat exchange plate.

In some embodiments of the invention a plurality of the thermally conductive members have thermally conductive pins, fins, bars or the like that project into the volume of a heat exchanger to form an efficient heat exchange interface with heat exchange fluid in the volume. The projecting pins, fins, bars, plates or the like that form a heat exchange interface with the fluid inside the volume of a heat exchanger may or may not be similar in shape or other physical characteristics to the pins, fins, bars, plates or the like that extend through the flexible medium to form a thermal channel through the medium.

The following example embodiments of the invention will be described in the context of cooling a living subject. Embodiments of the invention could also be applied to warming a subject.

Figure 1B:
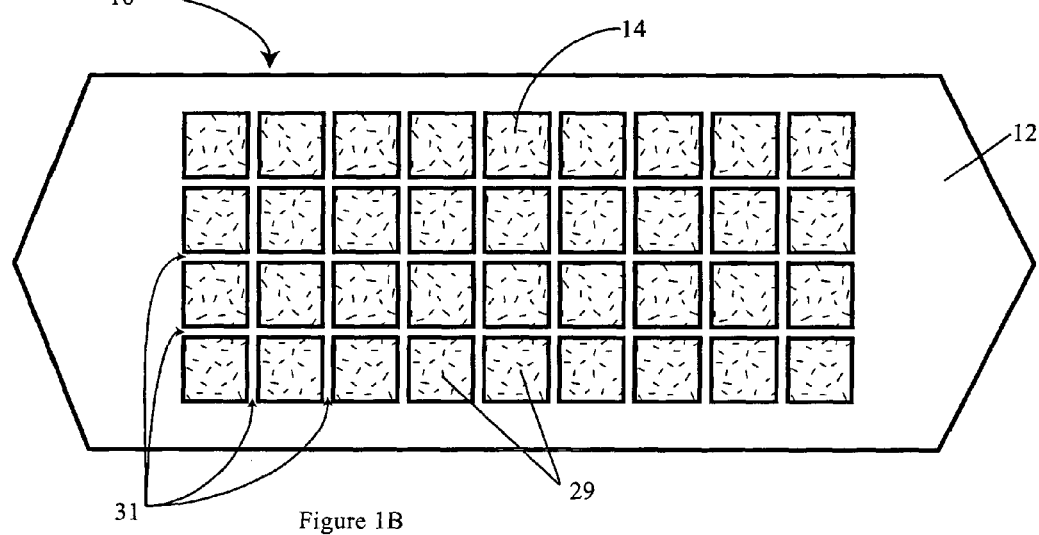
Figure 1C:
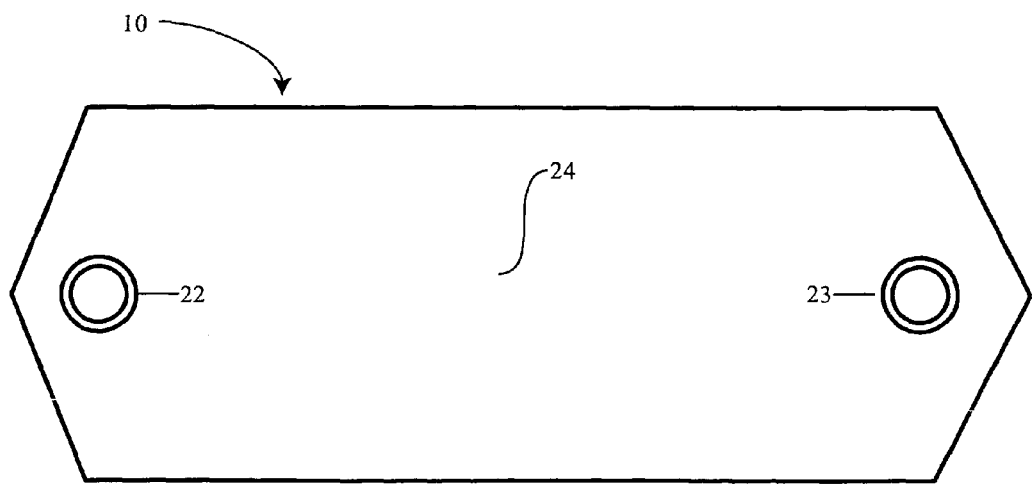

FIGS. 1A through 1C show a heat exchanger 10 according to an embodiment of the invention. Heat exchanger 10 has a flexible heat exchange plate 12 penetrated by a number of thermally conductive members 14. Plate 12 has an outer face 16 and an inner face 18. Heat exchanger 10 has an inside volume 20 and ports 22, 23 by way of which a heat exchange fluid can flow through volume 20. Volume 20 is defined on a front side by plate 12 and on a rear side by a rear wall 24. Side walls 25 extend between plate 12 and rear wall 24. Plate 12, rear wall 24 and side walls 25 are all flexible so that the outer surface 16 of heat exchanger 10 can conform to the local contours of a portion of a subject's anatomy.

Thermally conductive members 14 pass through the material 30 of plate 12. Inside ends 26 of thermally conductive members 14 project into volume 20. Ends 26 preferably project significantly into volume 20. In the illustrated embodiment, ends 26 are cut away to provide increased surface area for heat transfer with fluid in volume 20. Each inner end 26 comprises a number of prongs 27. Outer faces 28 of thermally conductive members can be placed against the skin of a subject. Outer faces 28 may be outer faces of bases 29. Bases 29 are separated sufficiently to permit heat exchanger 10 to flex in a desired degree but are preferably closely spaced to maximize the area of outer faces 28 that can be placed against a desired region on a subject. For example, in some embodiments, bases 29 are spaced apart from one another by spacings in the range of 0.5 mm to 5.0 mm.

In some embodiments, each base 29 has a thickness in the range of 0.5 mm to 5 mm. Preferably, base 29 has a thickness in the range of 1 mm to 2.5 mm. The size and dimensions of base 29 in the plane of plate 12 may be chosen to suit the application, and particularly depends on the contour of the object to be cooled or heated. Thermally conductive members 14 according to some embodiments of the invention for use in cooling/warming pads for human subjects, have bases 29 having areas in the range of 1 mm² to 400 mm². For such cooling/heating pads the area is preferably in the range of 10 mm² to 100 mm².

Thermally conductive members 14 may have reduced cross sectional areas in their portions inside bases 29. The cross-sectional area of thermally conductive members 14 at the point that thermally conductive members 14 emerge from material 30 on the inside face of plate 12 may, for example, be in the range of 20% to 100%, and preferably 35% to 65%, of the area of base 29.

Plate 12 comprises a flexible membrane through which thermally conductive members 14 project. The membrane may be made of a flexible material or materials 30. Thermally conductive members have lengths sufficient to pass through material 30. In preferred embodiments, members 14 project into volume 20. Thermally conductive members 14 may, for example, project into volume 20 for a distance in the range of 0 mm to 20 mm. In some embodiments intended for warming or cooling a living subject, thermally conductive members 14 project into volume 20 for a distance in the range of 2 mm to 10 mm. In some embodiments members 14 project past material 30 by at least 3 mm. The portions of members 14 which project into volume 20 may also function as supports to maintain a minimum spacing between wall 24 and plate 12.

It is not necessary that all thermally conductive members 14 be identical or that all thermally conductive members 14 have equal-sized bases 29 although it is convenient to make heat exchanger 10 with thermally conductive members 14 substantially the same as one another.

In some embodiments, rear wall 24 is made of material 30. Substantially all of heat exchanger 10, except for thermally conductive members 14, may be made of the same material or materials 30. Material 30 is preferably both flexible and elastically stretchable. Material 30 may, for example, comprise any of a variety of suitable flexible polymers such as natural rubber, polyurethane, polypropylene, polyethylene, ethylene-vinyl acetate, polyvinyl chloride, silicone, a combination of these materials or the like. Material 30, or portions of material 30 may optionally be loaded with particles of one or more thermally conductive materials such as metal or graphite. However, since material 30 is not required to play a significant role in conducting heat, material 30 may be a material having a low thermal conductivity not exceeding 5 $Wm^{-1}K^{-1}$ without significantly impairing the function of heat exchanger 10. In some embodiments, material 30 has a hardness in the range of 10 to 80 on the Shore A hardness scale.

One specific example embodiment of the invention is constructed as shown in FIGS. 1A to 1C and is designed to be applied to the neck of a human subject to cool the subject's brain. This embodiment of heat exchanger 10 has approximately 50 thermally conductive members 14 arranged in a rectangular array. Each member 14 has nine pins which project into volume 20. Bases 29 have areas of about 10 mm×10 mm and thicknesses of about 2 mm. Each of the pins has a diameter of about 1.8 mm. The total length of each of the pins is about 10 mm. The thickness of material 30 in the walls of heat exchanger 10 is about 4 mm. Two short acrylic tubes of approximately 10 mm inner diameter provide inlet and outlet ports 22 and 23. Cold water may be used as a cooling fluid.

Two such heat exchangers may be dimensioned so that they can be applied to a subject's neck respectively over the left and right carotid arteries to cool the subject's brain by cooling blood flowing to the subject's brain. The heat exchangers are sufficiently flexible to conform substantially to the curvature of the subject's neck without causing unacceptable pressure spots. The heat exchangers may be held in place under a collar, such as a foam collar.

Plate 12 may be fabricated using any suitable process. For example, plate 12 may be made by making holes in a sheet of material 30 and inserting thermally conductive members 14 through the holes. The holes may initially have dimensions smaller than corresponding dimensions of thermally conductive members 14 so that material 30 seals around thermally conductive members 14 sufficiently to prevent any significant loss of heat exchange fluid from volume 20. Additionally, or in the alternative, a sealant, such as a suitable glue may be provided to enhance the seal between thermally conductive members 14 and material 30. Plate 12 may also be made by a suitable plastic manufacturing process such as thermal injection molding, reaction injection molding, compression molding, vacuum forming or casting. In this case, thermally conductive members 14 may be molded into plate 12.

The thickness of material 30 in plate 12 can be selected to provide a desired compromise between flexibility and durability. Since heat exchanger 10 does not rely on material 30 to conduct heat, it is not necessary to make material 30 extremely thin to improve heat conduction. Material 30 may, for example, have a thickness in the range of about 1 mm to 20 mm. In some currently preferred embodiments of the invention, material 30 has a thickness in the range of 4 mm to 7 mm in plate 12. When thermally conductive members of the type shown in FIG. 4I to FIG. 4L are used, the thickness of material 30 may be smaller, for example, as little as about 1 mm in plate 12.

Projections of material 30 or some other material may optionally extend into volume 20. Such projections may be positioned to support wall 24 relative to plate 12, to direct the flow of fluid 65 within volume 20 and/or to induce turbulence at selected locations in the flow of fluid 65 in order to provide enhanced thermal contact between thermally conductive members 14 and fluid 65.

Figure 2D:
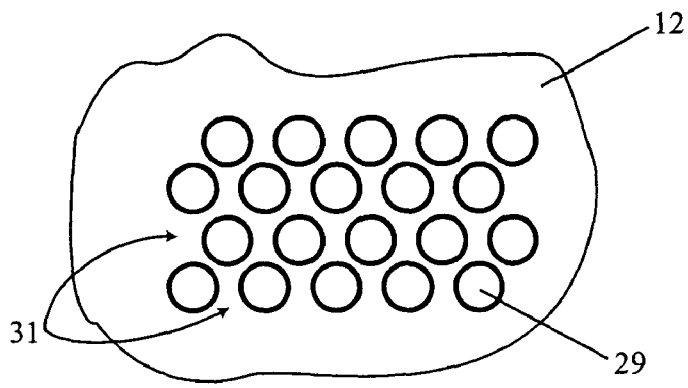
FIG. 2D is a partial view of the outside surface of a heat exchanger having thermally conductive members arranged in a triangular array.

Thermally conductive members 14 may be arranged in a wide range of patterns. For example, as shown in FIGS. 1A to 1C and 3A to 3C, members 14 may be arranged in a number of rows and columns to form a rectangular array, which could be a square array. In some embodiments, members 14 are arranged in rows or columns which are shifted relative to one another as shown in FIGS. 2B and 2C. This arrangement creates increased turbulence in fluid flowing through volume 20 and hence increases the efficiency of heat transfer between the inside ends of thermally conductive members 14 and fluid 65. In some embodiments, bases of members 14 are arranged in a rectangular array as illustrated, for example, in FIG. 1, while portions of members 14 which project into volume 20 are arranged in rows or columns which are shifted relative to one another as shown in FIGS. 2B and 2C. In some embodiments, members 14 are arranged in a triangular array, as shown in FIG. 2D.

Figure 2E:
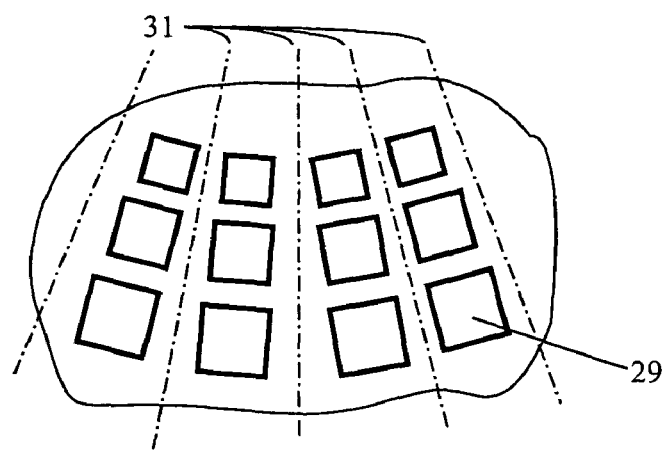
FIG. 2E is a partial view of the outside surface of a heat exchanger having thermally conductive members arranged to provide converging lines of flexible material.
Figure 2F:
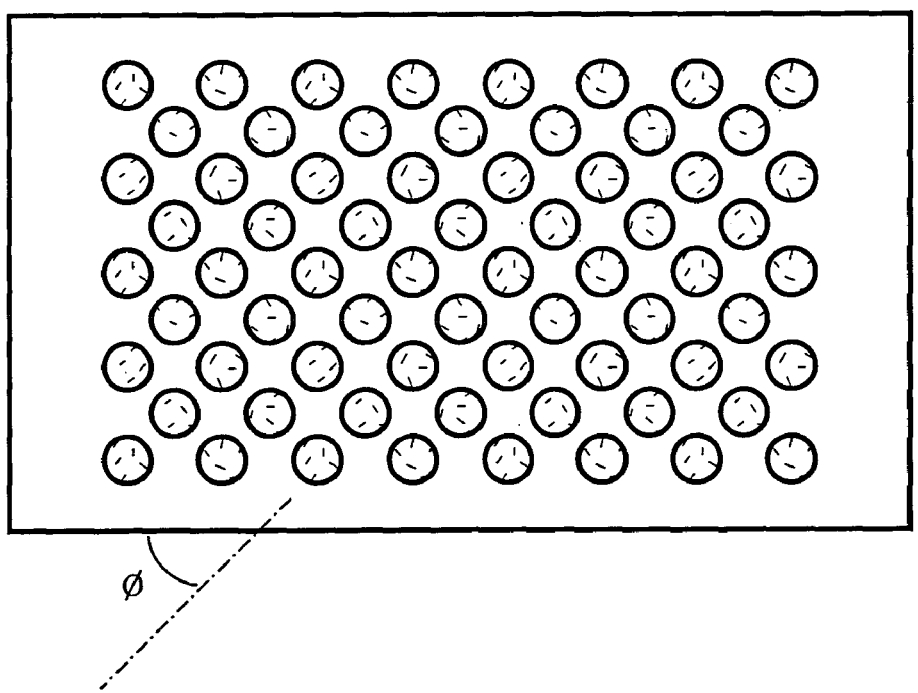
FIG. 2F is a view of the outside surface of a heat exchanger having thermally conductive members arranged in a rectangular array oriented at an angle to a long axis of the heat exchanger.

Flexing of plate 12 may be facilitated by arranging members 14 to provide substantially unbroken lines 31 of material 30 extending generally parallel to one or more axes about which a user may wish to flex heat exchanger 10. The embodiment shown in FIG. 1B shows two sets of lines 31 of material 30 which extend between adjacent rows and columns of members 14. The embodiment illustrated in FIG. 2B has one set of parallel lines 31. Lines 31 are not necessarily parallel to one another. For example, FIG. 2E illustrates an arrangement of members 14 which facilitates flexing in such a way as to conform to a portion of the surface of a cone. The array of members 14 is not necessarily aligned with any axis of heat exchanger 10. For example, FIG. 2F shows the outside face of a heat exchanger wherein thermally conductive members 14 are arranged in a rectangular array oriented at an angle, ϕ, to a long axis of the heat exchanger.

Figure 3A:
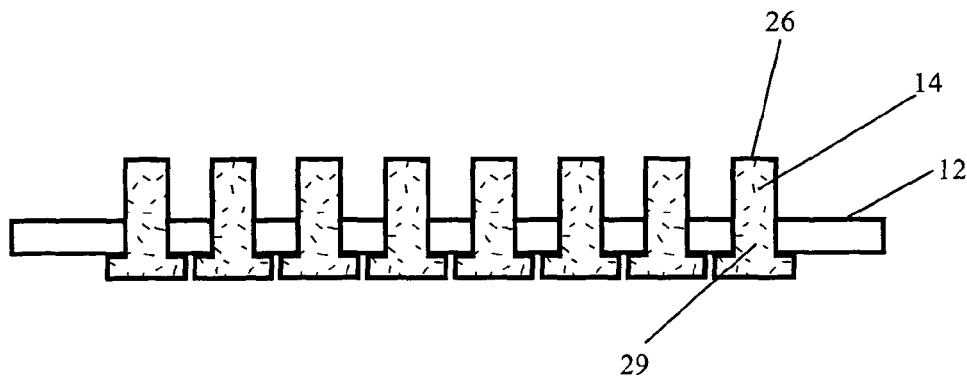
FIGS. 3A, 3B and 3C are respectively a cross-section view; a bottom view; and a top view of the flexible heat exchange plate of a heat exchanger according to one embodiment of the invention.
Figure 3B:
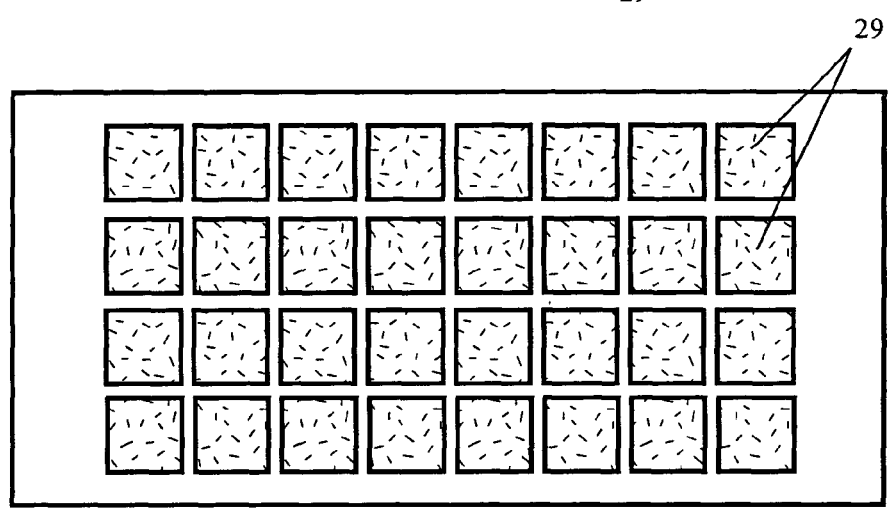
Figure 3C:
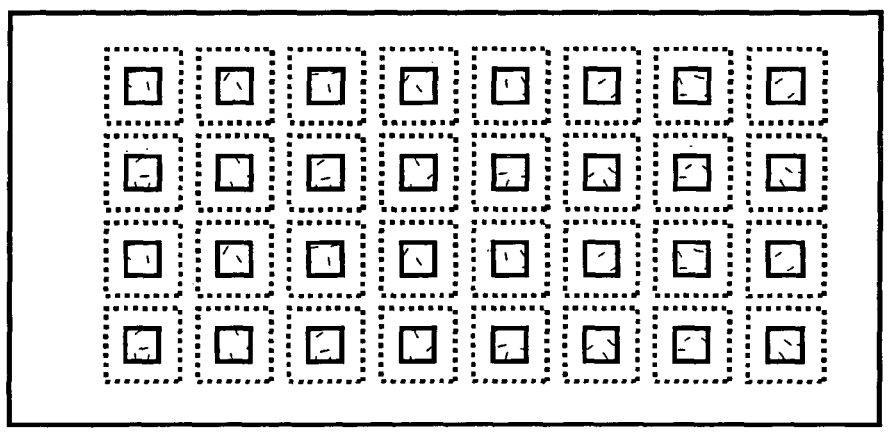

FIGS. 1A to 1C and 2A to 2F illustrate heat exchangers in which faces 28 are substantially flush with material 30 on outer face 16. This arrangement facilitates cleaning, as outer face 16 is substantially smooth. FIGS. 3A to 3C illustrate an alternative embodiment of the invention wherein base 29 is not embedded in material 30. The embodiments illustrated in these Figures can be fabricated by inserting thermally conductive members 14 though holes formed in a sheet of material 30.

Thermally conductive members 14 may take any of a wide variety of forms which provide the function of carrying heat in either direction between a subject on one side of the flexible plate and a heat exchange fluid or other matter on an opposed side as the flexible plate that is warmer or cooler than the subject. Ideally, members 14 provide good thermal interfaces between the thermally conductive members and the subject to be cooled or warmed; good thermal channels across flexible material 30; and good thermal interfaces between the thermally conductive members and the fluid in volume 20 of the thermal exchanger. Some possible forms for members 14 are illustrated in FIGS. 4A through 4L. It is understood that these are possible forms and are included only as examples. Modifications to these examples can be made to obtain a much larger list of examples. In addition, features illustrated in these examples can be exchanged or combined partially or fully to obtain an even larger list of examples.

Figure 4A:
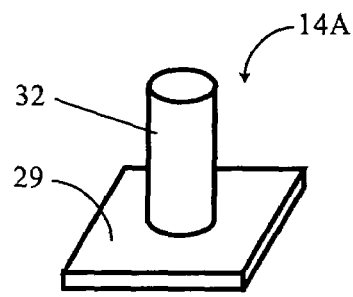
FIGS. 4A through 4L are views of different heat conductors that can be used in heat exchangers according to different embodiments of the invention.
Figure 4B:
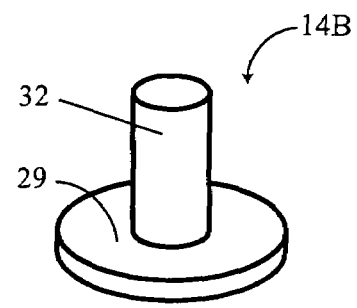

FIG. 4A shows a thermally conductive member 14A having a square base 29 and cylindrical pin 32. Pin 32 can carry heat through material 30 and constitute a means for channeling heat through flexible material 30 and releasing heat into (or taking heat from) fluid in volume 20 of a heat exchanger. FIG. 4B shows a thermally conductive member 14B having a circular base 29 instead of a square base.

Figure 4C:
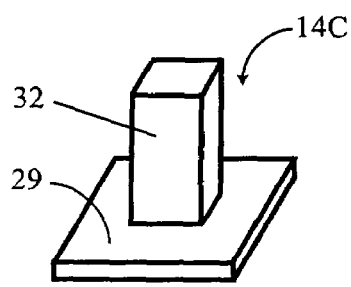
Figure 4D:
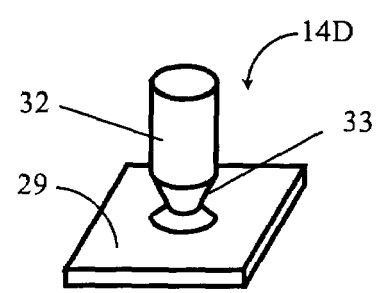
Figure 4E:
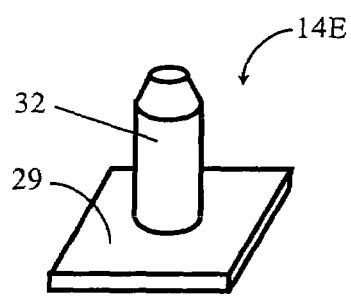

FIG. 4C shows a thermally conductive member 14C wherein both base 29 and the pin 32 are square in cross-section (like the thermally conductive members of FIGS. 2A to 2C). FIG. 4D shows a thermally conductive member 14D similar to member 14A except that pin 32 has a circumferential groove 33 in its part close to base 29. Groove 33 receives extra material 30 in an injection molding or casting process to better seal member 14D to material 30. FIG. 4E shows a thermally conductive member 14E wherein a tip of pin 32 is tapered to facilitate insertion into a hole in a sheet of material 30.

Figure 4F:
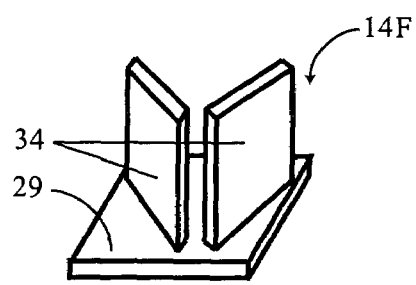

FIG. 4F shows a thermally conductive member 14F having a pair of platelike rectangular conductors 34 which serve both as thermal channels through material 30 and as structures for releasing heat into (or taking heat from) volume 20. Conductors 34 may be arranged in a V-shape to better transfer heat to fluid flowing past plates 34. Plate-like conductors could also be arranged in other manners such as being parallel with each other. Thermally conductive member 14F has the advantage in manufacturing that it can be made by cutting and folding thermally conductive sheet material.

Figure 4G:
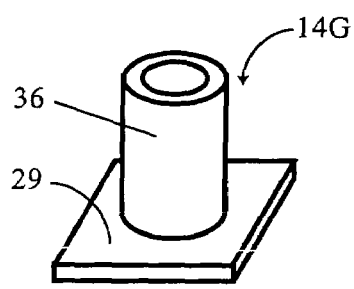
Figure 4H:
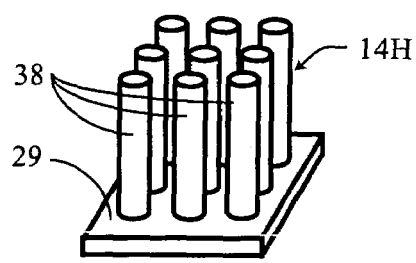
Figure 4I:
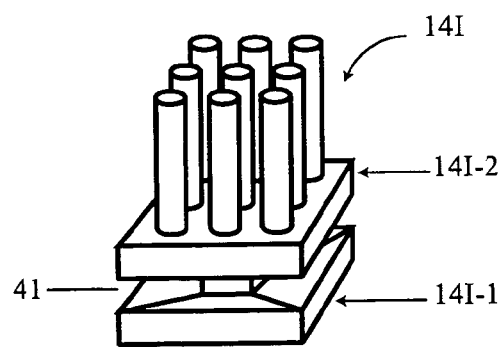
Figure 4J:
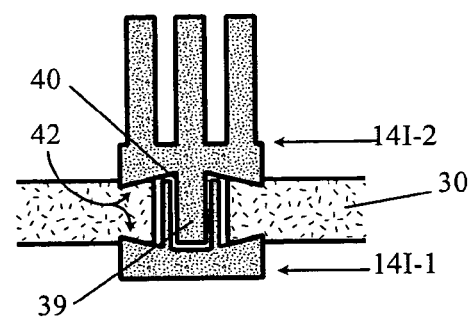
Figure 4K:
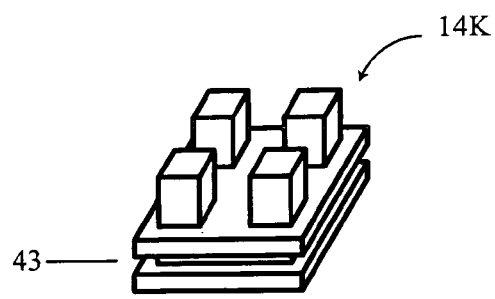
Figure 4L:
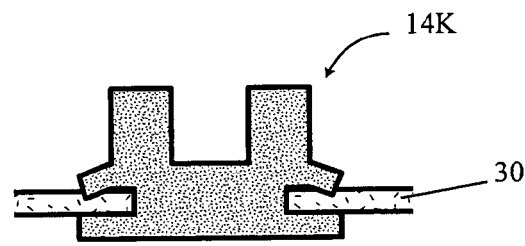

FIG. 4G shows a thermally conductive element 14G having a thermal channel portion provided by a tubular pin 36. FIG. 4H shows a thermally conductive member 14H having multiple pins 38 extending from base 29. Pins 38 provide multiple thermal channels extending from the same base 29 and projecting into the volume 30. Conductive member 14H advantageously provides increased contact area between conductive member 14H and a heat transfer fluid in volume 20. FIGS. 4I and 4J show a thermally conductive member 14I that is designed to reduce the possibility of fluid leaking between material 30 and member 14I. Member 14I may be fabricated in two-pieces 14I-1 and 14I-2 that can be assembled together in a manner that provides good thermal contact between pieces 14I-1 and 14I-2. In the illustrated embodiment, one of the pieces of member 14I has a pin 39 which is received in a corresponding socket 40 (see FIG. 3J) in the other piece. Pin 39 may have an interference fit in socket 40 to keep the two pieces tightly together and to provide good heat transfer between the pieces. A circumferentially extending groove 41 is defined between pieces 14I-1 and 14I-2. Groove 41 receives material 30. The faces of pieces 14I-1 and 14I-2 which contact material 30 may be undercut to provide ridges 42 which help to prevent fluid from leaking past member 14I. The pieces of multi-piece thermally conductive members may be fastened together in other ways which provide thermal contact between the pieces. For example, fastening means such as screws, rivets, or the like may be provided. FIGS. 4K and 4L show a thermally conductive member 14K that is similar to member 14I but is an integral part. Member 14K is designed to be cramped onto material 30. Material 30 projects into a groove 43. The sides of the groove 43 may be cramped together to hold material 30 around the edges of member 14K as shown in FIG. 4L.

Figure 5A:
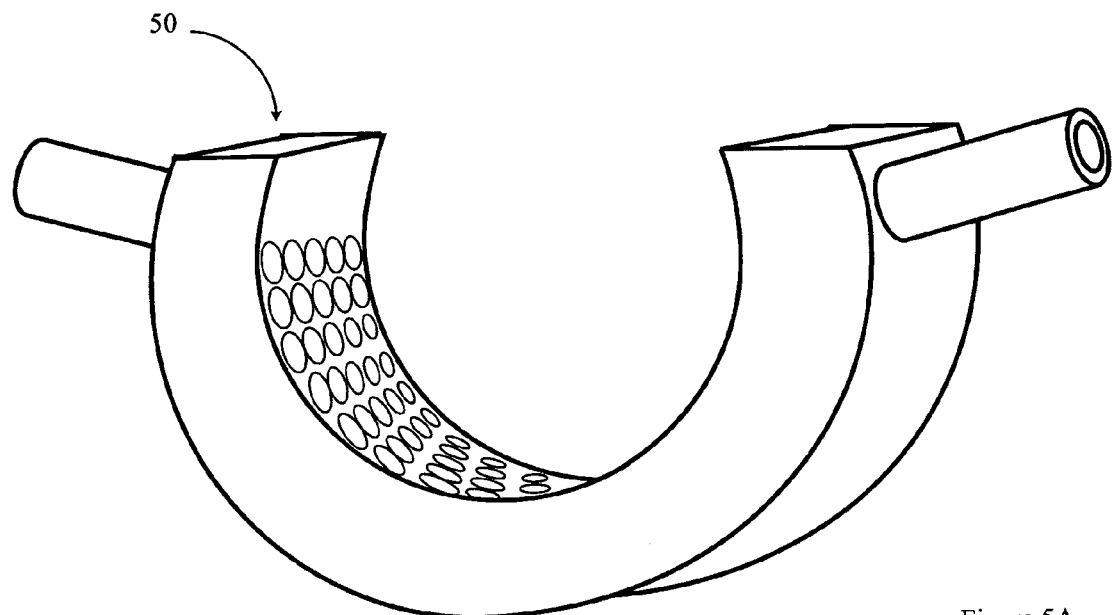
FIGS. 5A and 5B are respectively sectional and bottom views of a flexible plate of a heat exchanger according to another embodiment of the invention.
Figure 5B:
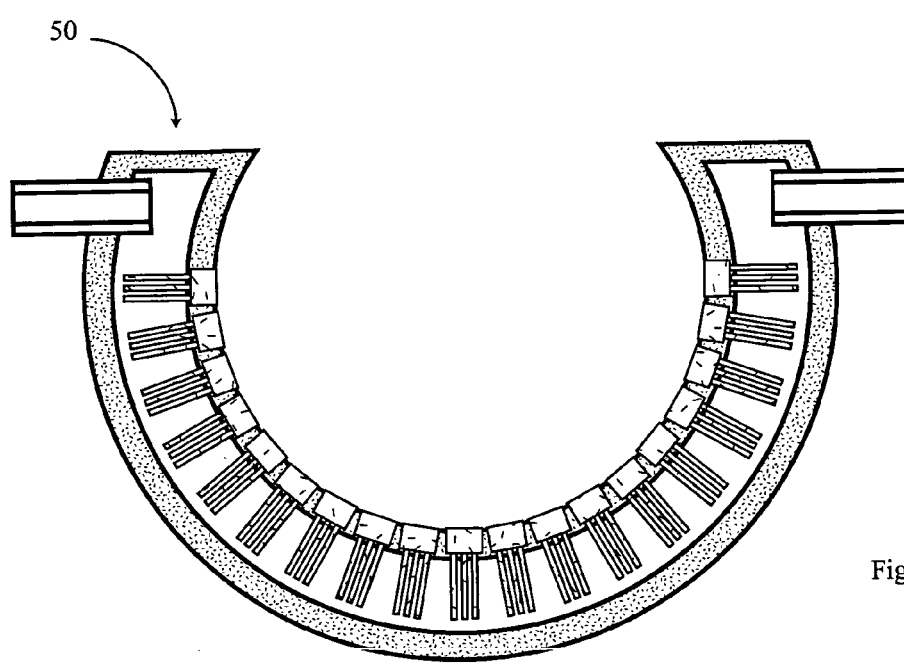

FIGS. 5A and 5B show a flexible fluid heat exchanger 50 which is normally curved in the absence of applied forces. Heat exchanger 50 may be used to apply heat to or to cool a substantially cylindrical object such as a subject's limb. Apart from being curved, heat exchanger 50 is similar to heat exchanger 10 of FIGS. 1A through 1C.

A suitable circulation system may be used to circulate a heat exchange fluid through the volume 20 of one or more heat exchangers as described herein. For cooling purposes it is desirable that the temperature of circulating fluid 65 be greater than 0° C. to avoid freezing the subject's skin. The desired temperature of the circulating fluid will depend to some degree on the application and the portion of the subject's body to be treated. The desired temperature for cold therapy ranges between 0° C. and 15° C. Water has properties which make it good for use as a circulating fluid 65.

It is generally desirable to maintain the pressure of fluid in volume 20 approximately equal to the air pressure surrounding heat exchanger 10. If the pressure within volume 20 is significantly smaller than the ambient air pressure then pressure differences across the walls of volume 20 will tend to collapse volume 20 although the projected ends 26 of thermally conductive members 14 may prevent the walls from complete collapse. If the pressure within volume 20 is significantly larger than the ambient air pressure then heat exchanger 10 will tend to balloon.

Figure 6:
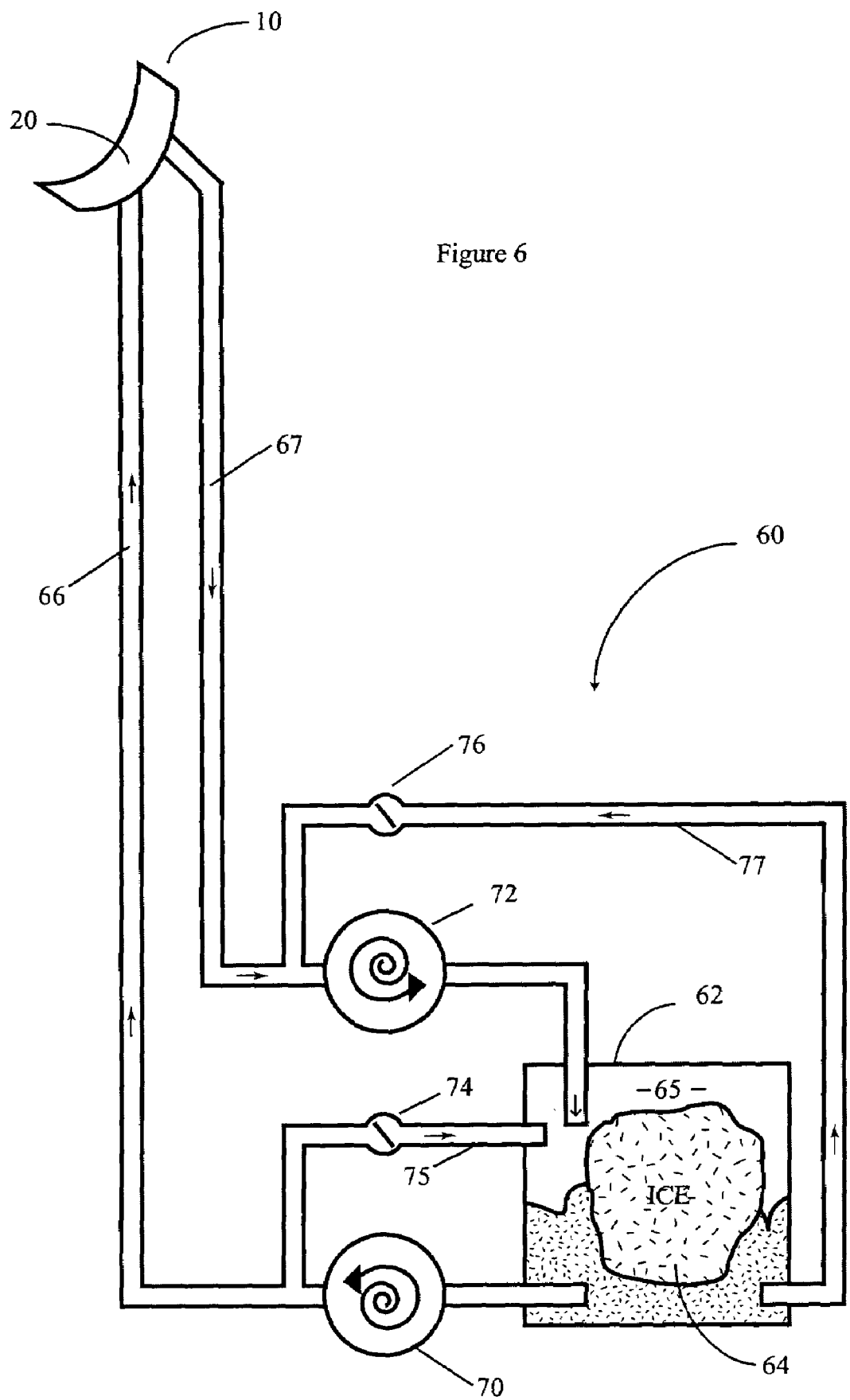
FIGS. 6, 7 and 8 are schematic views of cooling systems according to the invention.

FIG. 6 is a schematic view of a cooling system which includes a heat exchanger 10 and a fluid circulating system 60. Circulation system 60 has an insulated reservoir 62 containing a volume of ice 64. System 60 contains a suitable heat exchange fluid 65, which may be liquid water. System 60 delivers fluid 65 to heat exchanger 10 through delivery conduit 66 and returns coolant to reservoir 62 through a return conduit 67.

A first feed pump 70 upstream from heat exchanger 10 delivers fluid 65 from reservoir 62 to heat exchanger 10. A second feed pump 72 is located downstream from heat exchanger 10. Second feed pump 72 draws fluid 65 from heat exchanger 10 and returns the fluid to reservoir 62. First and second feed pumps 70 and 72 are balanced so that within volume 20 of heat exchanger 10 the pressure of fluid 65 is substantially equal to the ambient air pressure.

One or more bypass valves may be provided to provide better control over fluid pressure within volume 20. In system 60, an adjustable bypass valve 74 is connected between the output of first feed pump 70 and reservoir 62. Bypass valve 74 indirectly regulates the pressure within volume 20. When bypass valve 74 is opened, a larger proportion of fluid 65 is returned to reservoir 62 by way of bypass conduit 75 and the amount of fluid 65 flowing into heat exchanger 10 is reduced. Bypass valve 74 may be pressure-operated.

System 60 has a second bypass valve 76 connected in parallel with second feed pump 72. When second bypass valve 76 is open, second feed pump 72 can draw fluid 65 from reservoir 62 by way of conduit 77. Opening second bypass valve 76 increases pressure at the input of second feed pump 72 and consequently increases the pressure within volume 20.

Many variations of system 60 are possible. Although two bypass valves are shown in FIG. 6 for maximum flexibility, one bypass valve connected parallel with either one of pumps 70 or 72 or in parallel with heat exchanger 10 may be sufficient to permit pressure inside heat exchanger 10 to be maintained within a desired range. In addition, depending upon the construction of pumps 70 and 72 and the fluid flow properties of the circuit which includes conduits 66, 67 and heat exchanger 10 it may be possible to maintain the fluid pressure in volume 20 within the desired range without the need for bypass valves 74 and 76. Where bypass valves are provided it is not necessary that they be connected directly to reservoir 62 as illustrated. Other connections may be provided which have the result of maintaining pressures upstream and/or downstream from heat exchanger 10 at values which keep the pressure within volume 20 at a desired level while maintaining fluid flow through volume 20.

In some cases it may be convenient to provide a single reservoir 62 for providing heat exchange fluid for multiple heat exchangers 10. In such cases it is best to provide upstream and downstream pumps 70 and 72 for each heat exchanger 10. In the alternative, suitable manifolds, such as T-connectors, could be provided to allow a number of heat exchangers 10 to be connected in parallel between a single upstream pump system and a single downstream pump system.

Figure 7:
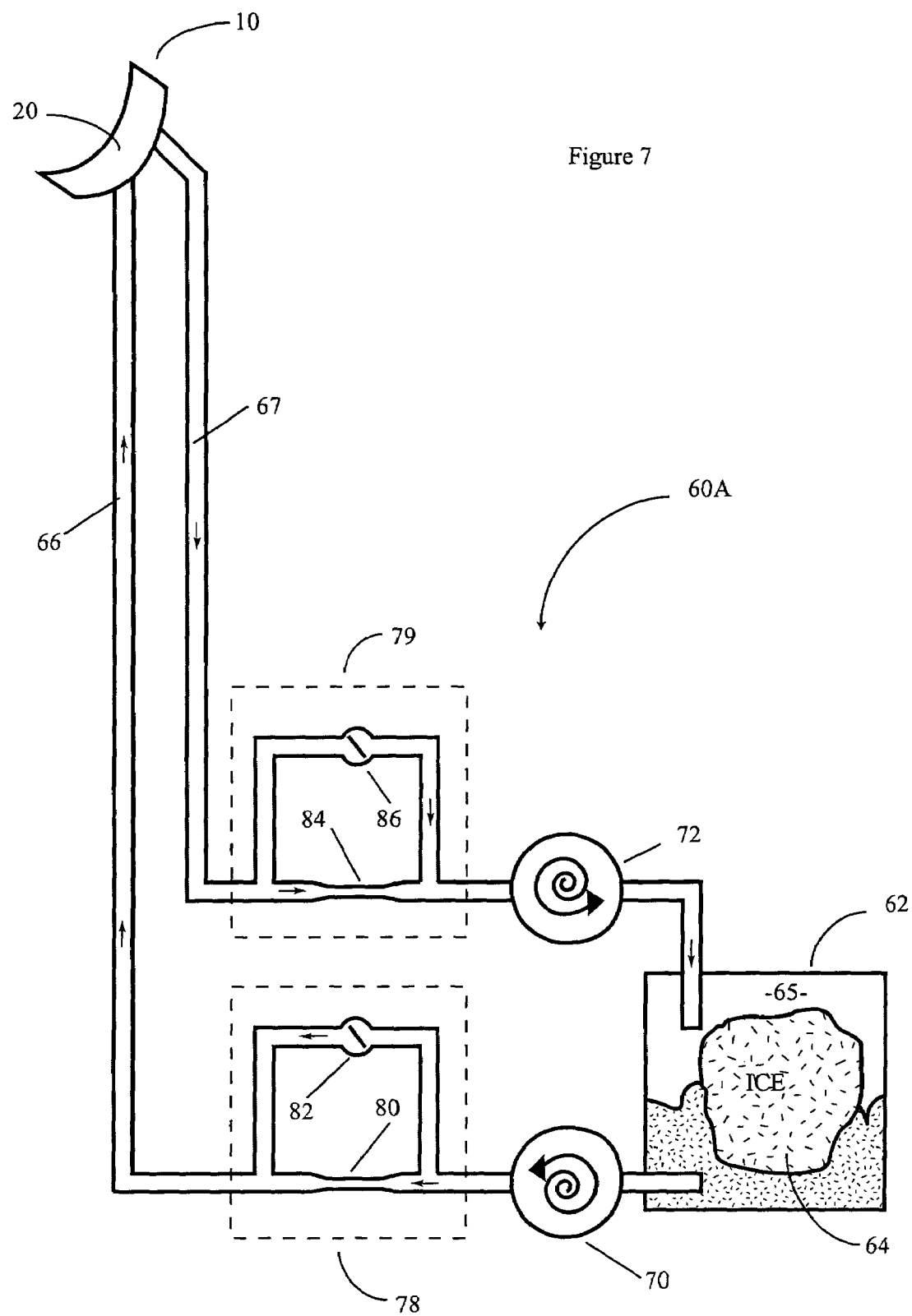

FIG. 7 illustrates another fluid circulating system 60A. In system 60A, a first flow regulator 78 comprising a restrictor 80 and a bypass valve 82 is provided between first feed pump 70 and heat exchanger 10. Bypass valve 82 is connected in parallel with restrictor 80. When fluid 65 is flowing through flow regulator 78 then a pressure drop across flow regulator 78 depends upon the fluid flow rate and upon the degree to which bypass valve 82 is open.

System 60A has a second flow regulator 79 which includes a second flow restrictor 84 and a bypass valve 86. Bypass valve 86 is connected in parallel with restrictor 84.

In system 60A, bypass valves 82 and 86 are adjustable. The fluid pressure within volume 20 can be controlled by adjusting one or both of bypass valves 82 and 86.

Some alternative embodiments of the invention lack one of flow regulators 78 and 79. When system 60A is connected to supply fluid 65 to a plurality of heat exchangers 10 it is preferable to provide for each heat exchanger 10 at least one adjustable flow regulator 78 or 79 located where only fluid going to or from that heat exchanger passes through the flow regulator. This permits the pressure within each heat exchanger 10 to be individually regulated. In the alternative, as described above, suitable manifolds may be provided to split the flow of fluid 65 between a number of heat exchangers 10 connected in parallel.

Figure 8:
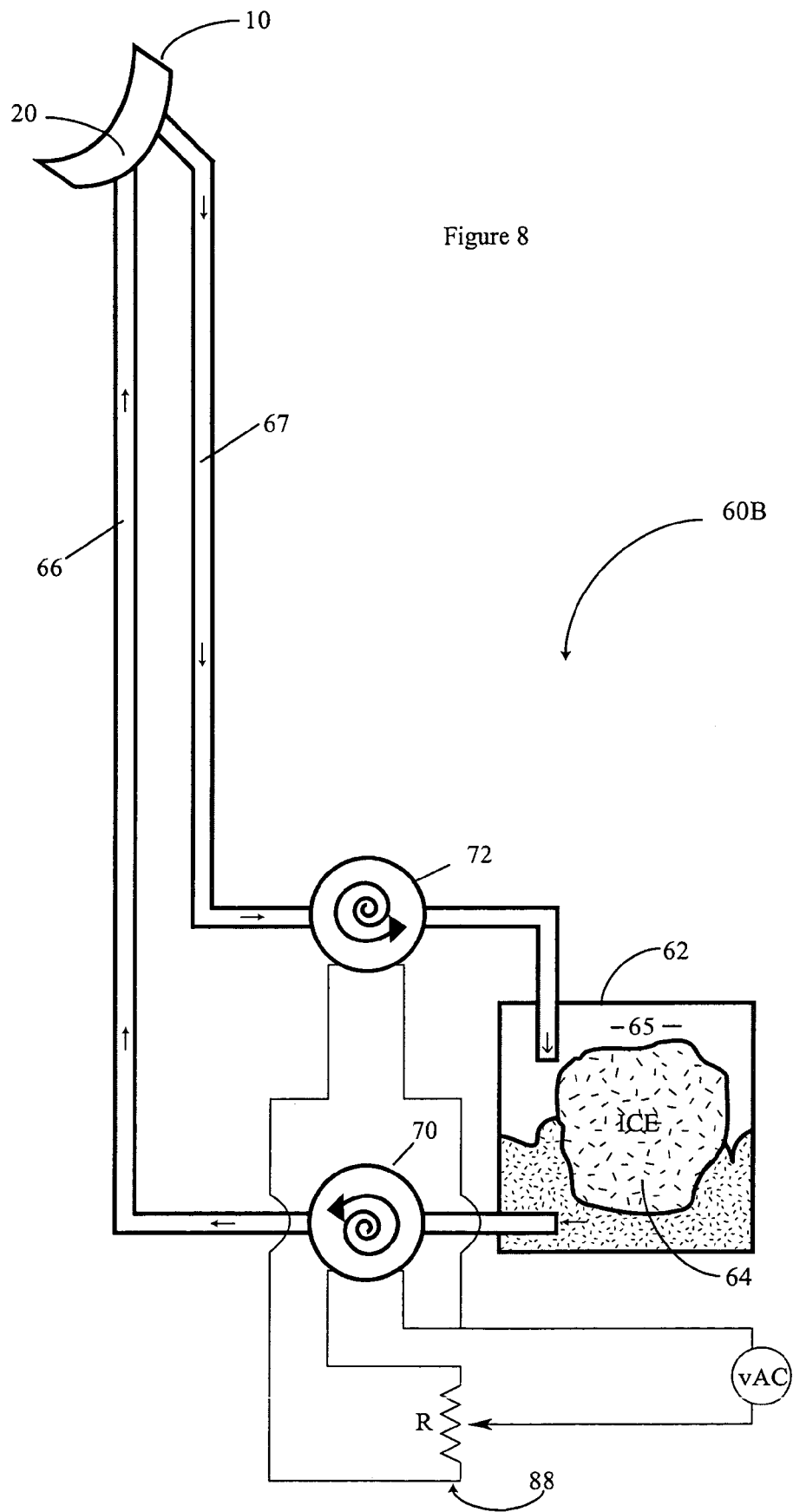

FIG. 8 illustrates another fluid circulating system 60B. In system 60B the pressure within volume 20 of heat exchanger 10 is controlled by adjusting the rate of operation of one or both of upstream and downstream feed pumps 70 and 72. In some embodiments of the invention a control system simultaneously increases the rate of operation of feed pump 70 and decreases the rate of operation of feed pump 72 or vice versa. The rate of operation of pumps 70 and 72 may be controlled by adjusting the rate of rotation of motors which drive the pumps, by adjusting displacements of the pumps, or the like.

In the illustrated embodiment, control is accomplished by operating a power splitter 88 (illustrated schematically by a potentiometer). Power splitter 88 can be operated to increase the speed of a motor driving pump 70 and to decrease the speed of a motor driving pump 72 or vice versa.

Systems 60, 60A and 60C may be automatically controlled using any suitable control system. For example, a controller may be provided to operate bypass valves and/or control pump speeds or displacements by way of suitable actuators (not shown) as necessary to control pressure within volume 20 to stay within a desired range. Those skilled in the art are familiar with suitable controllers. The controller may, for example, comprise a suitable programmed programmable controller or a hardware controller. One or more pressure sensors and/or flow sensors (not shown) may be included to provide feedback to the controller.

Any of cooling systems 60, 60A and 60B could be adapted for warming by replacing ice 64 with a suitable heating element which can be operated to raise fluid 65 in reservoir 62 to a desired temperature. Instead of ice 64, any of systems 60, 60A or 60B could cool fluid 65 by way of a refrigeration system. However, a refrigeration system large enough to provide high-rate cooling of a living person is expensive, consumes a large amount of power and is not readily portable. Ice has the advantage that melting a block of ice takes a large amount of heat. A reservoir 62 containing enough ice to apply high rate cooling to a human subject for a significant period can be small enough to be readily portable.

Where a component (e.g. a member, assembly, element, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example:

Thermally conductive members 14 may have any suitable shapes and arrangements. Those illustrated herein are but examples.

Flexible material 30 may have different compositions in different parts of a heat exchanger according to the invention. Different suitable flexible materials 30 may be used for material 30 in different parts of a heat exchanger.

A heat exchanger according to the invention is not necessarily rectangular or parallel-sided. A heat exchanger according to the invention could have other shapes. Heat exchangers according to some currently preferred embodiments of the invention are elongated and have fluid inlets and fluid outlets located in areas at opposed ends of a long axis.

Accordingly, the scope of the invention is to be construed in accordance with the substance defined by the following claims.

What is claimed is:

1. A flexible heat exchanger for warming or cooling a living subject, the heat exchanger comprising: a volume having at least one inlet for receiving a heat exchange fluid and at least one outlet; a flexible sheet-like heat exchange plate essentially impermeable to the heat exchange fluid, the plate comprising a plurality of substantially rigid thermally conductive members extending through a flexible material of the plate from an outer surface of the flexible material into the volume, wherein the thermally conductive members project into the volume and have bases that project past the outer surface of the flexible material; and wherein the volume is defined between the plate and a flexible sheet-like back wall spaced apart from the plate.

2. A flexible heat exchanger according to claim 1 wherein the thermally conductive members are arranged in a rectangular array.

3. A flexible heat exchanger according to claim 2 wherein the bases are generally rectangular.

4. A flexible heat exchanger according to claim 1 wherein the thermally conductive members are arranged in a triangular array.

5. A flexible heat exchanger according to claim 1 wherein the thermally conductive members are arranged to provide a plurality of substantially unbroken lines of the flexible material extending between the thermally conductive members.

6. A flexible heat exchanger according to claim 1 wherein the thermally conductive members each have a thermal conductivity of at least 50 $Wm^{-1}K^{-1}$.

7. A flexible heat exchanger according to claim 1 wherein the thermally conductive members each have a thermal conductivity of at least 100 $Wm^{-1}K^{-1}$.

8. A flexible heat exchanger according to claim 7 wherein the thermally conductive members are made of a material selected from the group consisting of: aluminum, copper, gold, silver, alloys of two or more of aluminum, copper, gold, or silver with one another and alloys of one or more of aluminum, copper, gold, or silver with one or more other metals.

9. A flexible heat exchanger according to claim 7 wherein the thermally conductive members are made of materials selected from the group consisting of: carbon, graphite, diamond, and sapphire.

10. A flexible heat exchanger according to claim 1 wherein the bases of the thermally conductive members cover at least 70% of an area of the outer surface of the flexible material of the flexible heat exchange plate.

11. A flexible heat exchanger according to claim 1 wherein the flexible material of the plate comprises an elastomer material and the thermally conductive members are embedded in the elastomer material.

12. A flexible heat exchanger according to claim 11 wherein the elastomer material comprises a material selected from the group consisting of: polyurethane, polypropylene, polyethylene, ethylene-vinyl acetate, polyvinyl chloride, silicone, natural rubber, and a combination of two or more of polyurethane, polypropylene, polyethylene, ethylene-vinyl acetate, polyvinyl chloride, and silicone.

13. A flexible heat exchanger according to claim 1 wherein the thermally conductive members project into the volume from an inner surface of the plate by distances of at least 3 mm.

14. A flexible heat exchanger according to claim 1 wherein the flexible material of the plate has a thermal conductivity not exceeding 5 $Wm^{-1}K^{-1}$.

15. A flexible heat exchanger according to claim 1 wherein the inner and of each of the plurality of thermally conductive members comprises a plurality of spaced apart projections.

16. A flexible heat exchanger according to claim 1 wherein a plurality of the thermally conductive members each comprise a first part connected to a second part wherein the first and second parts define a circumferentially extending groove and the flexible material of the plate is received in the groove.

17. A flexible heat exchanger according to claim 1 wherein an inner end of each of the thermally conductive members is tubular, square, rectangular, circular or spherical.

18. A flexible heat exchanger according to claim 1 wherein the outer surface has a concave curved configuration in the absence of bending forces acting on the heat exchanger.

19. A flexible heat exchanger according to claim 1 wherein the outer surface has a convex curved configuration in the absence of bending farces acting on the heat exchanger.

20. A flexible heat exchanger according to claim 1 wherein a portion of the outer surface of the heat exchanger on which the thermally conductive members are disposed is dimensioned to be applied exclusively to an area of a subject's anatomy overlying a carotid artery of the subject.

21. A flexible heat exchanger according to claim 1 wherein a total area of the thermally conductive members exposed on the outer surface of the flexible sheet-like heat exchange plate exceeds a total cross sectional area of the thermally conductive members at a point where the cross sectional members enter the volume.

22. A flexible heat exchanger according to claim 1 wherein the heat exchanger comprises spacing means for preventing the back wall from collapsing against the flexible plate.

23. A flexible heat exchanger according to claim 1 wherein the volume is defined between the flexible plate, a flexible rear wall made of the flexible material and flexible side walls made of the flexible material.

24. A system for controlling a temperature of a subject, the system comprising:
    a heat exchanger according to claim 1;
    a reservoir containing a heat exchange fluid;
    a first feed pump connected to feed heat exchange fluid from the reservoir into the inlet of the heat exchanger;
    a second feed pump connected to withdraw the heat exchange fluid from the outlet of the heat exchanger.

25. A system according to claim 24 comprising a controller connected to control operation of the first and second feed pumps to maintain a pressure of the heat exchange fluid within the volume within a desired range of an ambient air pressure outside the volume.

26. A system according to claim 25 comprising an adjustable bypass valve connected in parallel with one of the first and second feed pumps wherein the controller is configured to operate an actuator to adjust the bypass valve.

27. A system according to claim 24 comprising an adjustable bypass valve connected in parallel with one of the first and second feed pumps.

28. A system according to claim 27 wherein the adjustable bypass valve is configured to be opened by a pressure differential across the bypass valve.

29. A system according to claim 24 comprising a variable restriction connected between the heat exchanger and one of the feed pumps.

* * * * *